United States Patent [19]

Moroe

[11] Patent Number: 4,634,588
[45] Date of Patent: Jan. 6, 1987

[54] DEODORANT

[75] Inventor: Michio Moroe, Mitaka, Japan

[73] Assignee: Takasago Perfumery Co. Ltd., Tokyo, Japan

[21] Appl. No.: 741,560

[22] Filed: Jun. 5, 1985

[51] Int. Cl.$^4$ .......................... A61K 9/68; A61K 7/26
[52] U.S. Cl. ...................................... 424/48; 424/49; 424/58
[58] Field of Search ............................... 424/48, 49-58

[56] References Cited
FOREIGN PATENT DOCUMENTS
1098166 8/1958 Fed. Rep. of Germany ........ 424/58

Primary Examiner—Shep K. Rose
Attorney, Agent, or Firm—Cushman, Darby & Cushman

[57] ABSTRACT

Deodorant of natural origin, which is useful in the fields of foodstuff, cosmetics and toiletry. This deodorant is derived from brewed wine or residual fermentation materials produced in the manufacture of brewed wine. In one aspect, this deodorant is manufactured from the brewed wine by evaporating water and alcohols from the brewed wine to obtain residual product as a deodorant. In another aspect, the residual fermentation materials are first extracted with ethanol to obtain an ethanol-extracted liquid, which is then heated to evaporate water and alcohol therefrom to obtain the product. This deodorant may further contain amino acid and/or salts of amino acid.

10 Claims, No Drawings

DEODORANT

BACKGROUND OF THE INVENTION (a) Technical Field of the Invention

This invention relates to a deodorant derived from a natural product, and more particularly to a deodorant useful in the food and cosmetic industries.

(b) Description of the Prior Art

Active carbon and glyoxal are known to be useful as a deodorant in a various fields. While, 3,4-dihydro-2H-pyran derivatives, amylose and sodium-acrylate-acrylamide copolymer are known to be effective as a deodorant component in cosmetics.

In the food industry however, only a few materials such as dimethyl-amino allylsulfonate, acrylamide, glucosamine and cyclodextrin (which belongs to oligosaccharide and is employed as a foul breath-extinguishing agent) are known to be useful as a deodorant.

Under such a lag in the development of deodorant which is safe and effective in the food industry, a development of a new effective deodorant is highly solicited.

In view of these circumstances, the present inventor has made a many studies with a view to develop a deodorant of natural origin, which is sufficiently safe to health so as to applicable in the fields of food, cosmetics and toiletry. Meanwhile, the present inventor has noticed that sake (refined sake, synthesized sake) or wine, which is customary added as a seasoning in cooking fish or meat, is effective in improving not only the taste thereof, but also the smell of the cooked food. The present inventor has also noticed the fact that enzymes are capable of converting a bad smelling substance into an odorless substance through a biochemical process.

Taking these phenomena and facts into account, the present inventor has investigated various substances produced and handled in the brewing industry with a view to find out any suitable substance for a deodorant. As a result of the research, the present inventor has succeeded to find out a substance having a deodorizing property which is existed in the extracts of various brewed wines. This inventor's research has further continued on the practicability and utility of the substance having such a deodorizing property. As a result, it has been found that extracts from only limited kinds of the brewed wines are useful for a deodorant, and that a deodorant substance found in unrefined sake or raochu wine is too strong in odor to use as a deodorant in general. A distilled liquor such as low-class distilled spirits and whisky has also been found to be unsuitable as a raw material.

In Japan, fish or meat is cooked by adding thereto seasonings such as miso (fermented bean paste), soy sauce, kombu (sea weed) and pieces of dried bonito. These seasonings are indeed effective in improving the taste of a cooked food owing to the amino acid components contained therein. However, it has been found by the present inventor that some of these amino acid components are effective not only in improving the taste, but also in removing a bad smell of fish and meat.

Accordingly, a many number of amino acids have been examined by the present inventor with respect to their deodorizing effects, and as a result, specific amino acids have been found to have a prominent deodorizing effect.

Further, a combination of these specific amino acids has been found to have a synergistic deodorizing effect.

SUMMARY OF THE INVENTION

There are a variety of amino acids and salts thereof which are employed in this invention as follows for example. Conjugated amino acid such as l-arginine l-glutamate, l-lysine l-aspartate and l-lysine l-glutamate and so forth; sulfur-containing amino acid such as methionine and so forth; aromatic amino acid such as tryptophan, l-phenylalanine and so forth; dicarboxy-amino acid and salts thereof such as l-glutamic acid, sodium l-glutamate, l-sodium aspartate and so forth and; aliphatic amino acid and salts such as dl-alanine, l-isoleucine, glycine, threonine, l-theanine, l-valine, l-lysine and so forth.

According to this invention, there is provided a deodorant comprising as an effective component a residual substance (hereinafter referred to as an extract) which is obtained by removing water and alcohols from brewed wine or an ethanol-extracted liquid of a fermentation residue byproduced in the manufacture of the brewed wine.

In this specification, the definition of "brewed wine" or brewage wine includes Japanese wine, grape wine and beer. In this invention, an extract obtained by evaporating water and alcohols from the brewed wine is used as a deodorant. Further, an extract obtained by first extracting solid fermentation lees with ethanol, and then evaporating water and alcohol from the resultant extracted liquid can be also used as a deodorizing component. In this case, the solid fermentation lees which are useful in this invention includes those produced in the manufacturing process of brewage wine, such for example as sake lees produced in the manufacture of Japanese wine, seed husk and lees discharged in the manufacture of grape wine, and residue left after the filtration a fermented material in the manufacture of beer.

The evaporations of water and alcohols from the brewed wine can be conducted by the conventional method preferably under a reduced pressure of from 20 to 500 mmHg and at a temperature of from 30° to 95° C. (preferably, in a warm water bath) for a sufficient period of time to remove substantially all of water and alcohols. Extract thus obtained is oily or viscous material.

When the solid fermentation lees are employed as a raw starting material, (a volume of) ethanol weighing from half times to ten times of the solid lees is added therein and stirred for 0.5 to 2 hours, optionally in a heated condition. Subsequently, the resultant mixture is filtered to obtain an ethanol-extracted liquid. This extracted liquid is then treated in the same manner as above-described to remove substantially all of water and alcohol. Thus obtained product is also oily or viscous in general.

The extract obtained in this manner can be put in use as it is. However, the extract is generally used as a diluted liquid by adding thereto an organic solvent or water thereby adjusting the concentration of the extract to conform to its end use. For example, if the deodorant is desired to be used in food industry, the extract may be diluted with a solvent such as propylene glycol, glycerin or ethanol which is officially recognized as a food additive, or with water. While, if the deodorant is desired to be used in cosmetic industry, the extract may be diluted with a solvent such as ethanol of isopropanol, which is officially recognized as a cosmetic raw material, or with water.

The deodorant of this invention is very effective to various bad smelling substances such for example as ammonia, hydrogen sulfide, trimethylamine and methylmercaptan. In addition, since the deodorant of this invention is solely derived from natural products, it can be safely utilized without raising any problems.

Accordingly, the deodorant of this invention is applicable to oral hygiene products such as tooth paste, mouth wash, chewing gum, candies and the like; food additives such as fish/meat odor masking agent; cosmetics such as antiperspirant/deodorant agent, deodrant soap, shampoo, rinse, tonic and the like; washroom, garbage box, room deodor-fragrance agent, and other household products; bad-smell extinguishing agent for a factory; and other industrial applications. If desired, the deodorant of this invention can be used in combination with other deodorizing materials such as an extract from tea leaves, crushed grains of sake lees, L-ascorbic acid, benzoic acid, gluconic acid, folic acid, nicotinic acid, and other organic acids, dl-α-tocopherol, ester gum, and methyl hesperidin in comply with its specific use.

This invention will be further explained with reference to the following examples and application examples. However these examples should not be construed to limiting the scope of this invention.

The assessment tests of deodorant on bad smelling materials were conducted as follows.

METHOD OF MEASURING AMMONIA-REMOVAL RATIO

Test samples were prepared so that each raw deodorant weighed 1 g and were introduced respectively into 100 ml vial to be subsequently sealed therein. Then gas containing 2.1 g of ammonia was injected into the vial by a gas-tight syringe. The vials were then kept at room temperature for a predetermined period of time.

Then 0.3 ml of gas in the vial was taken out of the vial and introduced into gas-chromatograph. On the other hand, a control vial containing a standardized gas and being sealed was prepared. In the same manner as mentioned above, a gas sample in the control vial was taken out and introduced into gas-chromatograph. The ammonia-removal ratios (%) of the test samples were determined from the measurements of the samples and the control.

The operation of the gas-chromatograph was conducted in the following conditions.

Filler: "Chromosorb 103" (80/100)
Separation tube: 3 mm in inner diameter, 2 m in length, made of glass
Temperature: 140° C. at the separation tube, 150° C. at inlet, and 150° C. at detector
Carrier Gas: He 2 kg/cm$^2$
Electrometer: Attenuation 2, Electric current 100 mA
Feeding Speed of Recording Paper: 10 mm/min.
Apparatus: Shimazu GC-7A
Detector: TCD

METHOD OF MEASURING TRIMETHYLAMINE-REMOVAL RATIO

Test samples were prepared so that each raw deodorant weighed 1 g and were introduced respectively into 100 ml vial to be subsequently sealed therein. Then gas containing 1.9 mg of trimethyl-amine was injected into the vial by a gas-tight syringe. Then almost the same procedure was repeated as in the measurement of ammonia-removal.

The operation of the gas-chromatograph was conducted in the following conditions.

Filler: "Chromosorb 103" (80/100)
Separation tube: 3 mm in inner diameter, 2 m in length, made of glass
Temperature: 180° C. at the separation tube, 250° C. at inlet, and 250° C. at detector
Carrier Gas: N$_2$ 2 kg/cm$^2$
Gas Pressure: H$_2$ 0.6 kg/cm$^2$ air 0.5 kg/cm$^2$
Electrometer: Attenuation 32, Range 10$^2$
Feeding Speed of Recording Paper: 10 mm/min.
Apparatus: Shimazu GC-7A
Detector: FID

METHOD OF MEASURING HYDROGEN SULFIDE-REMOVAL RATIO

Test samples were prepared so that each raw deodorant weighed 1 g and were introduced respectively into 100 ml vial to be subsequently sealed therein. Then gas containing 1.7 ml of hydrogen sulfide was injected into the vial by a gas-tight syringe. Then almost the same procedure was repeated as in the measurement of ammonia-removal.

The operation of the gas-chromatograph was conducted in the following conditions.

Filler: 30% TCEP on Chromosorb WAW (60/80)
Separation tube: 3 mm in inner diameter, 3 m in length, made of glass
Temperature: 45° C. at the separation tube, 100° C. at inlet, and 100° C. at detector
Carrier Gas: He 0.8 kg/cm$^2$
Electrometer: Attenuation 8, Electric current 125 mA
Feeding Speed of Recording Paper: 10 mm/min.
Apparatus: Shimazu GC-7A
Detector: TCD

METHOD OF MEASURING METHYLMERCAPTAN-REMOVAL RATIO

Test samples were prepared so that each raw deodorant weighed 1 g and were introduced respectively into 100 ml vial to be subsequently sealed therein. Then gas containing 0.89 mg of methylmercaptan was injected into the vial by a gas-tight syringe. Then almost the same procedure was repeated as in the measurement of ammonia-removal.

The operation of the gas-chromatograph was conducted in the following conditions.

Filler: 30% TCEP on Chromosorb WAW (60/80)
Separation tube: 3 mm in inner diameter, 2 m in length, made of glass
Temperature: 120° C. at the separation tube, 250° C. at inlet, and 250° C. at a detector
Carrier Gas: N$_2$ 0.7 kg/cm$^2$
Gas pressure: H$_2$ 0.5 kg/cm$^2$, air 1.0 kg/cm$^2$
Electrometer: Range 32, Sensitivity 10$^2$
Feeding Speed of Recording Paper: 10 mm/min.
Apparatus: Shimazu GC-4CM
Detector: FID

EXAMPLE 1

540 ml of red wine ("MANNS WINE" (trade mark), a product of KIKKOMAN CORPORATION) were introduced into a rotary evaporator and distilled in a warm water bath (90° C.) under a reduced pressure of 30 mmHg for 3 hours to evaporate water and alcohol contained in the red wine. As a result, 14.9 g of red viscous extract was obtained. This extract smelled wine-like fragrance and refreshing sourness. This extract was diluted to a concentration of 10% by adding propylene glycol and offered for a deodorizing test. The result was as shown in Tables 2 to 5.

EXAMPLE 2

540 ml of rose wine ("MANNS WINE" (trade mark), a product of KIKKOMAN CORPORATION) were treated in the same manner as Example 1 to obtain 12.0 g of red viscous extract having a smell of wine-like fragrance and refreshing sourness. This extract was diluted to a concentration of 10% by adding propylene glycol and offered for a deodorizing test. The result was as shown in Tables 2 to 5.

EXAMPLE 3

540 ml of white wine ("MANNS WINE" (trade mark), a product of KIKKOMAN CORPORATION) were treated in the same manner as Example 1 to obtain 11.1 g of yellow brown viscous extract having a weak wine-like fragrance and refreshing sourness which was more mild as compared with that of the extract obtained from the red wine. This extract was diluted to a concentration of 10% by adding thereto propylene glycol and then offered for a deodorizing test. The result was as shown in Tables 2 to 5.

EXAMPLE 4

The procedure of Example 1 was repeated except that 600 ml of Japanese sake ("NIHONSAKARI" (trade mark), 2nd grade, a product of NISHINOMIYA SHUZO Co., Ltd.) was employed as a raw starting material. As a result, 9.2 g of light yellow viscous extract having rice-like flavor and amino acid-like taste was obtained. This extract was diluted to a concentration of 10% by adding thereto propylene glycol and then offered for a deodorizing test. The result was as shown in Tables 2 to 5.

EXAMPLE 5

The procedure of Example 1 was repeated except that 720 ml of beer (a product of KIRIN BREWERY Co., Ltd.) was employed as a raw starting material. As a result, 1.8 g of light yellow viscous extract having a weak straw-like smell and a refreshing bitterness was obtained. This extract was diluted to a concentration of 10% by adding thereto propylene glycol and then offered for a deodorizing test. The result was as shown in Tables 2 to 5.

EXAMPLE 6

To 500 g of lees from red wine brewage (a residue removed of liquid by wine press in subsequent to the fermentation step) were added 500 g of ethanol and then stirred for two hours. Then, the mixture was vacuum-filtered through a G-3 glass filter to obtain an ethanol-extracted liquid. This liquid was then distilled at 70° C./30 mmHg for two hours to evaporate water and alcohol contained in the liquid. As a result, 5.0 g of red oily extract having a weak wine-like fragrancy and a refreshing sourness was obtained. This extract was diluted to a concentration of 10% by adding thereto propylene glycol and offered for a deodorizing test. The result was as shown in Tables 2 to 5.

EXAMPLE 7

To 500 g of sake lees on the market were added 500 g of ethanol and they were mixed together for two hours. Then, the subsequent procedures of Example 6 were repeated to obtain 10.1 g of yellow viscous extract having a flavor of lightly fermented rice and amino acid-like taste. This extract was diluted to a concentration of 10% by adding thereto propylene glycol and offered for a deodorizing test. The result was as shown in Tables 2 to 5.

EXAMPLES 8 TO 26

Amino acids and salts thereof were diluted with water or ethanol to obtain solutions as indicated in Table 1, and each solution was offered for a deodorizing test. The results were as shown in Tables 2 to 5.

TABLE 1

| Examples | Compound | Solution |
| --- | --- | --- |
| 8 | l-Sodium Aspartate | 10% aq. solution |
| 9 | dl-Alanine | 10% aq. solution |
| 10 | l-Arginine l-Glutamate | 10% aq. solution |
| 11 | Isoleucine | 4% aq. solution |
| 12 | Glycine | 10% aq. solution |
| 13 | Glutamic Acid | 10% ethanol solution |
| 14 | Sodium Glutamate | 10% aq. solution |
| 15 | dl-Threonine | 10% aq. solution |
| 16 | l-Threonine | 10% aq. solution |
| 17 | l-Theanine | 10% aq. solution |
| 18 | dl-Tryptophan | 10% ethanol solution |
| 19 | l-Tryptophan | 10% ethanol solution |
| 20 | l-Valine | 10% aq. solution |
| 21 | l-Phenylalanine | 3% aq. solution |
| 22 | dl-Methionine | 5% aq. solution |
| 23 | l-Methionine | 5% aq. solution |
| 24 | l-Lysine l-Aspartate | 5% aq. solution |
| 25 | l-Lysine hydrochloride | 10% aq. solution |
| 26 | l-Lysine l-Glutamate | 5% aq. solution |

EXAMPLE 27

7 parts by volume of 10% propylene glycol solution of the extract obtained in Example 4 were mixed with 3 parts by volume of 10% aqueous solution of sodium glutamate obtained in Example 14 to obtain a mixed solution. This mixed solution was then offered for a deodorizing test. The result was as shown in Experiments 1 and 2.

EXAMPLE 28

8 parts by volume of 10% propylene glycol solution of the extract obtained in Example 6 were mixed with two parts by volume of 10% aqueous solution of l-valine obtained in Example 20 to thereby form a mixed solution. This mixed solution was then offered for a deodorizing test. The result was as shown in Experiments 1 to 3.

EXAMPLE 29

7 parts by volume of 10% propylene glycol solution of the extract obtained in Example 3 were mixed with 3 parts by volume of 5% aqueous solution of l-lysine l-glutamate obtained in Example 26 to thereby form a mixed solution, which was then offered for a deodorizing test. The result was as shown in Experiments 3 to 4.

COMPARATIVE EXAMPLE 1 g of active carbon ("Kimco" (trade mark), a product of American Drug Corp., which is used for refrigerator as a deodorant) was offered for a deodorizing test. The result was as shown in Table 2 to 5.

TABLE 2

(Ammonia Removal Ratio (%))

| Samples | Test Time (minutes) | | | | |
|---|---|---|---|---|---|
| | 1 | 3 | 5 | 10 | 20 |
| Example 1 | 62 | 85 | 100 | | |
| Example 2 | 58 | 72 | 90 | 100 | |
| Example 3 | 52 | 78 | 91 | 100 | |
| Example 4 | 30 | 42 | 56 | 72 | 78 |
| Example 5 | 28 | 42 | 53 | 59 | 72 |
| Example 6 | 45 | 72 | 85 | 100 | |
| Example 7 | 21 | 35 | 42 | 62 | 80 |
| Example 8 | 86 | 99 | 100 | | |
| Example 9 | 84 | 98 | 100 | | |
| Example 10 | 85 | 92 | 100 | | |
| Example 11 | 90 | 98 | 100 | | |
| Example 12 | 89 | 98 | 100 | | |
| Example 13 | 100 | | | | |
| Example 14 | 100 | | | | |
| Example 15 | 90 | 98 | 100 | | |
| Example 16 | 90 | 98 | 100 | | |
| Example 17 | 100 | | | | |
| Example 18 | 90 | 97 | 100 | | |
| Example 19 | 89 | 96 | 100 | | |
| Example 20 | 89 | 97 | 100 | | |
| Example 21 | 90 | 99 | 100 | | |
| Example 22 | 89 | 94 | 100 | | |
| Example 23 | 90 | 96 | 100 | | |
| Example 24 | 86 | 99 | 100 | | |
| Example 25 | 82 | 92 | 100 | | |
| Example 26 | 98 | 100 | | | |
| Comparative Example | 12 | 25 | 40 | 52 | 60 |
| Control* | 8 | 12 | 12 | 28 | 32 |

*propylene glycol

TABLE 3

(Trimethylamine Removal Ratio (%))

| Samples | Test Time (minutes) | | | | |
|---|---|---|---|---|---|
| | 1 | 3 | 5 | 10 | 20 |
| Example 1 | 62 | 90 | 100 | | |
| Example 2 | 60 | 85 | 92 | 100 | |
| Example 3 | 59 | 95 | 100 | | |
| Example 4 | 51 | 62 | 80 | 100 | |
| Example 5 | 40 | 55 | 65 | 86 | 100 |
| Example 6 | 46 | 90 | 100 | | |
| Example 7 | 59 | 61 | 72 | 100 | |
| Example 8 | 92 | 100 | | | |
| Example 9 | 95 | 100 | | | |
| Example 10 | 99 | 100 | | | |
| Example 11 | 92 | 100 | | | |
| Example 12 | 95 | 100 | | | |
| Example 13 | 100 | | | | |
| Example 14 | 100 | | | | |
| Example 15 | 90 | 100 | | | |
| Example 16 | 93 | 100 | | | |
| Example 17 | 92 | 100 | | | |
| Example 18 | 93 | 100 | | | |
| Example 19 | 90 | 100 | | | |
| Example 20 | 93 | 100 | | | |
| Example 21 | 95 | 100 | | | |
| Example 22 | 89 | 100 | | | |
| Example 23 | 90 | 100 | | | |
| Example 24 | 79 | 100 | | | |
| Example 25 | 89 | 100 | | | |
| Example 26 | 100 | | | | |
| Comparative Example | 8 | 31 | 52 | 70 | 86 |
| Control* | 12 | 15 | 15 | 27 | 31 |

*propylene glycol

TABLE 4

(Hydrogen Sulfide Removal Ratio (%))

| Samples | Test Time (minutes) | | | | |
|---|---|---|---|---|---|
| | 1 | 3 | 5 | 10 | 20 |
| Example 1 | 52 | 75 | 83 | 100 | |
| Example 2 | 32 | 60 | 75 | 92 | 100 |
| Example 3 | 42 | 70 | 80 | 95 | 100 |
| Example 4 | 32 | 57 | 62 | 70 | 85 |
| Example 5 | 18 | 32 | 73 | 73 | 75 |
| Example 6 | 62 | 89 | 92 | 100 | |
| Example 7 | 45 | 59 | 62 | 72 | 86 |
| Example 8 | 8 | 15 | 17 | 32 | 56 |
| Example 9 | 10 | 15 | 17 | 31 | 59 |
| Example 10 | 12 | 15 | 19 | 30 | 70 |
| Example 11 | 8 | 14 | 19 | 21 | 82 |
| Example 12 | 25 | 30 | 35 | 24 | 89 |
| Example 13 | 26 | 31 | 32 | 46 | 100 |
| Example 14 | 11 | 15 | 19 | 48 | 100 |
| Example 15 | 8 | 12 | 17 | 21 | 92 |
| Example 16 | 10 | 13 | 14 | 24 | 89 |
| Example 17 | 12 | 18 | 30 | 62 | 95 |
| Example 18 | 11 | 17 | 19 | 31 | 97 |
| Example 19 | 10 | 12 | 20 | 26 | 92 |
| Example 20 | 8 | 14 | 20 | 28 | 85 |
| Example 21 | 7 | 11 | 14 | 25 | 83 |
| Example 22 | 9 | 11 | 14 | 30 | 92 |
| Example 23 | 8 | 11 | 15 | 30 | 84 |
| Example 24 | 10 | 12 | 16 | 32 | 95 |
| Example 25 | 10 | 12 | 16 | 35 | 96 |
| Example 26 | 18 | 22 | 28 | 39 | 82 |
| Comparative Example | 7 | 20 | 35 | 58 | 60 |
| Control* | 12 | 12 | 14 | 27 | 29 |

*propylene glycol

TABLE 5

(Methylmercaptan Removal Ratio (%))

| Samples | Test Time (minutes) | | | | |
|---|---|---|---|---|---|
| | 1 | 3 | 5 | 10 | 20 |
| Example 1 | 35 | 56 | 72 | 80 | 89 |
| Example 2 | 52 | 62 | 75 | 87 | 92 |
| Example 3 | 19 | 18 | 25 | 56 | 89 |
| Example 4 | 17 | 19 | 70 | 71 | 72 |
| Example 5 | 19 | 32 | 45 | 52 | 63 |
| Example 6 | 45 | 57 | 71 | 80 | 90 |
| Example 7 | 19 | 28 | 50 | 52 | 62 |
| Example 8 | 15 | 23 | 28 | 52 | 72 |
| Example 9 | 18 | 18 | 22 | 24 | 62 |
| Example 10 | 20 | 24 | 32 | 45 | 62 |
| Example 11 | 12 | 18 | 20 | 27 | 65 |
| Example 12 | 11 | 17 | 20 | 42 | 80 |
| Example 13 | 9 | 14 | 18 | 42 | 90 |
| Example 14 | 25 | 30 | 42 | 72 | 82 |
| Example 15 | 18 | 20 | 24 | 28 | 62 |
| Example 16 | 7 | 13 | 25 | 32 | 85 |
| Example 17 | 9 | 18 | 20 | 42 | 85 |
| Example 18 | 10 | 18 | 19 | 50 | 62 |
| Example 19 | 11 | 18 | 30 | 42 | 80 |
| Example 20 | 13 | 14 | 15 | 60 | 92 |
| Example 21 | 14 | 18 | 20 | 42 | 75 |
| Example 22 | 10 | 13 | 15 | 35 | 70 |
| Example 23 | 11 | 18 | 22 | 45 | 62 |
| Example 24 | 11 | 18 | 20 | 25 | 82 |
| Example 25 | 12 | 18 | 35 | 42 | 75 |
| Example 26 | 32 | 36 | 41 | 62 | 82 |
| Comparative Example | 10 | 10 | 12 | 28 | 45 |
| Control* | 11 | 12 | 17 | 20 | 21 |

*propylene glycol

EXPERIMENT 1

10% of propylene glycol solutions of extracts obtained in Examples 1 to 5 as well as solutions of Examples 27 and 28 were employed in the manufacture of chewing gums as illustrated below.

Thereby sensitivity tests for assessing deodorizing effects on foul breath by using the chewing gum were conducted. As a result, these tests demonstrated excellent effects of the deodorants as indicated in Table 6.

The assessment on the foul breath extinguishing effect was carried out as follows.

In order to totally examine the foul breath extinguishing effect, sensitivity tests in vitro were conducted on an artificial foul breath, a smoking odor and a garlic odor. In producing the artificial foul breath, three main foul breath components, i.e. hydrogen sulfide, methylmercaptan and dimethyl sulfide were employed in the following preparation procedure.

(1) A hydrogen sulfide gas was saturated into 200 ml of pure water at a temperature of 15° C. taking about one hour.

(2) 100 ml of the resultant hydrogen sulfide-saturated solution were mixed with 200 mg of dimethyl sulfide and 200 mg of methylmercaptan to produce an artificial foul breath solution.

This artificial foul breath solution was diluted with pure water at a ratio of 1:100 (the foul breath solution:-pure water). Then, panelists rinsed their mouth with this diluted solution, and immediately after the rinsing 3 l of breathed air were collected in a bag (a product of OHMI ODOR AIR SERVICE Co., Ltd). This collected breath was provisionally determined as assessment value "0". Thereafter, the above chewing gums each containing deodorant component of this invention were taken into the mouths of the panelists to continuously chew the gums for three minutes and then 3 l of breathed air were again taken out for the assessment.

The smoking odor was prepared by employing three pieces of cigaret and each piece of cigaret was smoked using the same holder ("FRIEND HOLDER" (trade mark), a product of LOTTE ELECTRONICS INDUSTRIAL Co., Ltd.) until it is shortened to a length of 2 cm as measured from the filter portion of the cigaret. The time limit of smoking three pieces of the cigaret was set to 3 minutes. Upon finishing the smoking, 3 l of breathed air were collected into a bag, setting the assessment value as "0". Then the chewing gums each containing deodorant component of this invention were continuously chewed by the panelists for 3 minutes and then 3 l of breathed air were again taken out for the assessment.

The garlic odor was prepared by introducing into a mortar 50 g of minced garlic (which is produced by first slicing garlic and subsequently crushing it to a grain diameter of 2 to 3 mm after drying the sliced garlic), adding 200 ml of warm water (about 40° C.), mashing the mixture for 10 minutes, filtering the mixture using gauze as a filter to obtain 160 g of garlic extract and diluting the extract with pure water to increase the volume 20 times larger. 10 ml of this diluted garlic liquid is taken into the mouths of panelists for 5 minutes, and then 3 l of breathed air were collected in a bag, setting the assessment value as "0". Then, the chewing gums each containing deodorant of this invention were continuously chewed by the panelists for 3 minutes and then 3 l of breathed air were again taken out for the assessment.

The assessment of deodorizing effect was carried out by five experienced panelists in accordance with the following method. The assessment was classified into 5 steps in accordance with assessed points.

| Assessment Points | Expression of Intensity | Intensity of Odor |
| --- | --- | --- |
| 0 | Immediately after the generation of foul breath produced by this experiment | Very strong |
| 1 | Concentration of 1/10 of "0" | Strong |
| 2 | Concentration of 1/100 of "0" | Easily recognizable |
| 3 | Concentration of 1/300 of "0" | recognizable |
| 4 | Concentration of 1/1000 of "0" | Hardly recognizable |

| Composition of Chewing Gum | |
| --- | --- |
| Gum base | 20% (weight) |
| Sugar | 60% (weight) |
| Corn Syrup | 15% (weight) |
| Water | 4% (weight) |
| Deodorant | 1% (weight) |

TABLE 6

| | Foul Breath-Removal Effect | | |
| --- | --- | --- | --- |
| Samples | Artificial Foul Breath | Smoking Odor | Garlic Odor |
| Example 1 | 3.6 | 3.5 | 3.2 |
| Example 2 | 3.5 | 3.0 | 3.1 |
| Example 3 | 3.1 | 3.2 | 2.8 |
| Example 4 | 2.8 | 3.0 | 2.5 |
| Example 5 | 2.9 | 2.9 | 3.0 |
| Example 27 | 3.0 | 3.1 | 2.7 |
| Example 28 | 3.7 | 3.6 | 3.3 |
| Control* | 2.4 | 2.6 | 1.3 |

*Chewing gum containing no deodorant. The content of water is increased to 5%.

EXPERIMENT 2

10% propylene glycol solutions of extracts obtained in Examples 1 to 5 as well as solutions of Examples 27 and 28 were employed in the manufacture of mouth washes as illustrated below.

| Composition Of Mouth Washes | |
| --- | --- |
| Water | 80% |
| Deodorant | 10% |
| Ethanol | 10% |

Assessment method of the mouth washes was conducted in the same manner as in Experiment 1. The results were as shown in Table 7.

TABLE 7

| | Deodorizing Effect Of Mouth Washes | | |
| --- | --- | --- | --- |
| Samples | Artificial Foul Breath | Tobacco Odor | Garlic Odor |
| Example 1 | 3.7 | 3.6 | 3.8 |
| Example 2 | 3.5 | 3.6 | 3.7 |
| Example 3 | 3.1 | 3.1 | 3.5 |
| Example 4 | 2.9 | 2.6 | 3.1 |
| Example 5 | 2.8 | 2.4 | 2.6 |
| Example 27 | 3.0 | 2.8 | 3.2 |
| Example 28 | 3.6 | 3.5 | 3.8 |
| Control* | 1.6 | 1.0 | 1.2 |

*Only propylene glycol is employed

EXPERIMENT 3

Shampoo was manufactured by employing the solutions obtained in Examples 1, 28 and 29 and following components.

| | |
|---|---|
| Triethanol amine alkylsulfate | 14% |
| Monoethanol amine coconut oil fatty ester | 6% |
| Ethylene glycol monostearate | 1% |
| Deodorant | 1% |
| Water | 78% |

Assessment on the removal of sweaty odor by this shampoo was made according to the following method by ten experienced panalists in comparison with the control.

| | |
|---|---|
| Completely removed | +2 |
| Slightly removed | +1 |
| Unrecognizable | 0 |
| Sweaty odor is slightly recognized | −1 |
| Deodorizing effect is not recognized | −2 |

The results of these assessments were as shown in Table 8. From Table 8, it is apparent that the shampoo containing the deodorant of this invention is very effective in removing sweaty odor.

TABLE 8

| | Sweaty Odor-Removal Effect | | | | | | | | | | |
|---|---|---|---|---|---|---|---|---|---|---|---|
| Samples | A | B | C | D | E | F | G | H | I | J | average |
| Example 1 | +1 | +2 | +2 | +1 | +1 | +1 | +1 | +1 | +2 | +1 | +1.3 |
| Example 28 | +2 | +2 | +2 | +1 | +1 | +1 | +1 | +1 | +1 | +2 | +1.4 |
| Example 29 | +1 | +1 | +2 | +2 | +1 | +2 | +2 | +2 | +1 | +1 | +1.5 |
| Control* | +1 | +1 | 0 | 0 | 0 | 0 | +1 | 0 | −1 | −1 | +0.1 |

*Water was employed in lieu of deodorant of this invention

EXPERIMENT 4

Toilet deodorant (spray type) was manufactured by employing the solutions obtained in Examples 1, 2 and 29 and following components.

| | |
|---|---|
| Toilet deodorant (10% aq. solution) | 20% |
| Ethanol (95%) | 20% |
| Flon gas | 60% |

Assessment on the removal of toilet odor by this toilet deodorant was made according to the following method by ten experienced panalists.

The said deodorant was sprayed into a toilet of western style with a capacity of 2 m × 1 m × 2.5 m (5 m$^3$) for ten seconds, and the assessment before and after the spraying was made according to the following method.

| | |
|---|---|
| Completely removed | +2 |
| Slightly removed | +1 |
| Unrecognizable | 0 |
| Toilet odor is slightly recognized | −1 |
| Deodorizing effect is not recognized | −2 |

The results of these assessments were as shown in Table 9. From Table 9, it is apparent that the toilet deodorant containing the deodorant of this invention is very effective in removing toilet odor.

TABLE 9

| | Toilet Odor-Removal Effect | | | | | |
|---|---|---|---|---|---|---|
| Samples | A | B | C | D | E | average |
| Example 1 | +1 | +1 | +2 | +2 | +1 | +1.4 |
| Example 2 | +1 | +1 | +2 | +1 | +1 | +1.2 |
| Example 29 | +2 | +1 | 0 | +2 | +1 | +1.2 |
| Control* | +1 | 0 | 0 | −1 | −1 | −0.5 |

*Water was employed in lieu of deodorant of this invention

What is claimed is:

1. A chewing gum all but effective amount of having a wine like fragrance comprising as an effective component, extinguishing odor of foul breath components hydrogen sulfide, methylmercaptan and dimethy sulfide, smoking tobacco odor, garlic odor, sweaty odor, and toilet odor, a residual solid, oily or viscous substance which is obtained by removing water and alcohols from brewed wine or an ethanol-extracted liquid of a fermentation residue by-produced in the manufacture of the brewed wine.

2. A deodorant according to claim 1, wherein the brewed wine is selected from the group consisting of sake, grape wine and beer.

3. A deodorant according to claim 1, which further comprises amino acid salts of amino acid and mixtures thereof as another effective prominance synergist deodorizing component.

4. A deodorant according to claim 3, wherein the brewed wine is selected from the group consisting of sake, grape wine and beer.

5. A deodorant according to claim 3, wherein said another prominant synergistic deodorizing effective component is selected from the group consisting of conjugated amino acid, sulfur-containing amino acid, aromatic amino acid, dicarboxy-amino acid, aliphatic amino acid salts thereof and mixtures thereof.

6. A deodorant according to claim 4, wherein the conjugated amino acid is selected from the group consisting of 1-arginine 1-glutamate, 1-lysine 1-aspartate and 1-lysine 1-glutamate.

7. A deodorant according to claim 5, wherein said sulfur-containing amino acid is methionine.

8. A deodorant according to claim 5, wherein said aromatic amino acid is selected from the group consisting of tryptophan and 1-phenylalanine.

9. A deodorant according to claim 5, wherein said dicarboxyamino acid is selected from the group consisting of glutamic acid, sodium glutamate and 1-sodium aspartate.

10. A deodorant according to claim 5, wherein said aliphatic amino acid is selected from the group consisting of dl-alanine, 1-isoleucine, glycine, threonine, 1-theanine, 1-valine, 1-lysine mono hydrochloride.

* * * * *